(12) United States Patent
Bardo et al.

(10) Patent No.: US 11,166,681 B2
(45) Date of Patent: Nov. 9, 2021

(54) ADJUSTABLE COMPUTED TOMOGRAPHY HEAD FIXATOR FOR NEUROLOGICAL SCANS

(71) Applicant: Phoenix Children's Hospital, Inc., Phoenix, AZ (US)

(72) Inventors: Dianna Bardo, Phoenix, AZ (US); Molly Golek, Tempe, AZ (US); Charles Bolton, Tempe, AZ (US); Keawepono Wong, Tempe, AZ (US)

(73) Assignee: Phoenix Children's Hospital, Inc., Phoenix, AZ (US)

( * ) Notice: Subject to any disclaimer, the term of this patent is extended or adjusted under 35 U.S.C. 154(b) by 273 days.

(21) Appl. No.: 16/383,151

(22) Filed: Apr. 12, 2019

(65) Prior Publication Data

US 2019/0313985 A1 Oct. 17, 2019

Related U.S. Application Data

(60) Provisional application No. 62/657,579, filed on Apr. 13, 2018.

(51) Int. Cl.
*A61B 6/04* (2006.01)
*A61G 13/12* (2006.01)

(52) U.S. Cl.
CPC .......... *A61B 6/0421* (2013.01); *A61G 13/121* (2013.01)

(58) Field of Classification Search
CPC ....... A61B 6/0421; A61B 5/702; A61B 5/704; A61B 6/0407; A61B 6/0428;

(Continued)

(56) References Cited

U.S. PATENT DOCUMENTS 3,572,835 A * 3/1971 Kees, Jr. ................ A61G 13/12
297/410
4,616,814 A 10/1986 Harwood-Nash et al.
(Continued)

FOREIGN PATENT DOCUMENTS

CN 202288323 U 7/2012
CN 203914942 U 11/2014
(Continued)

OTHER PUBLICATIONS

IMRIS Inc., "IMRIS launches world's first MR-safe and CT-compatible neurosurgical horshoe headrest," www.newswire.ca/newsreleases/imris-launches-worlds-first-mrsafe-and-ct-compatible-neurosurgicalhorseshoe-headrest-513766811.html, Feb. 19, 2014.

(Continued)

*Primary Examiner* — Nicholas F Polito
*Assistant Examiner* — George Sun
(74) *Attorney, Agent, or Firm* — Messner Reeves LLP

(57) ABSTRACT

Systems and methods for securely positioning a patient's head during medical imaging are presented. A fixation device includes a headrest which may be provided with inflatable chambers to adjust the headrest to the patient's head, a neck section which may be adjustable, and a base designed to couple to a patient bed or gurney forming part of a medical imaging system. The fixation device allows adjustment of the patient's head to an orientation which may variously minimize scanning time, improve imaging results, and/or protect sensitive tissues from unnecessary irradiation.

10 Claims, 9 Drawing Sheets

(58) Field of Classification Search
CPC ...... A61B 6/0442; A61B 5/70; A61G 13/121; A61G 13/1205; A61G 13/1215; A61G 13/122; A61G 13/1225; A61G 13/123; A61G 13/1235; A61G 13/124; A61G 13/1245; A61G 13/125; A61G 13/1255; A61G 13/126; A61G 13/128; A61G 7/07; A61G 7/072; A61G 13/1265
See application file for complete search history.

(56) References Cited

U.S. PATENT DOCUMENTS

| | | | | |
|---|---|---|---|---|
| 5,147,287 | A * | 9/1992 | Jewell | A61G 13/12 5/622 |
| 5,807,255 | A | 9/1998 | Yokota et al. | |
| 6,460,207 | B1 * | 10/2002 | Papay | A47G 9/1009 5/603 |
| 6,557,195 | B2 * | 5/2003 | Dinkier | A61B 6/0442 5/601 |
| 6,684,431 | B2 | 2/2004 | Splane, Jr. | |
| 6,698,045 | B1 * | 3/2004 | Coppens | A61G 13/12 128/869 |
| 7,450,985 | B2 | 11/2008 | Meloy | |
| 7,451,507 | B2 * | 11/2008 | Brinkerhoff | A61G 13/12 5/637 |
| 7,909,036 | B2 | 3/2011 | Kusner, Jr. et al. | |
| 8,732,879 | B2 | 5/2014 | Patton et al. | |
| 8,887,331 | B2 | 11/2014 | Nakamura et al. | |
| 9,204,818 | B2 * | 12/2015 | Moffatt | A61B 6/4417 |
| 2001/0032364 | A1 * | 10/2001 | VanSteenburg | A61G 13/12 5/621 |
| 2002/0032927 | A1 * | 3/2002 | Dinkier | A61G 13/12 5/601 |
| 2005/0067875 | A1 * | 3/2005 | DeBraal | A61G 13/121 297/409 |
| 2005/0160532 | A1 * | 7/2005 | Froelich | A61G 13/12 5/637 |
| 2008/0078031 | A1 * | 4/2008 | Weinstein | A61F 5/3707 5/630 |
| 2009/0307845 | A1 * | 12/2009 | Rao | A61G 13/0072 5/622 |
| 2010/0147313 | A1 * | 6/2010 | Albrecht | A61G 13/12 128/845 |
| 2010/0211099 | A1 * | 8/2010 | Radermacher | A61G 13/12 606/245 |
| 2011/0035882 | A1 * | 2/2011 | Lijun | A61G 13/1235 5/601 |
| 2012/0124747 | A1 * | 5/2012 | Soto | A61G 13/101 5/622 |
| 2012/0124748 | A1 * | 5/2012 | Soto | A61G 13/121 5/640 |
| 2016/0151221 | A1 * | 6/2016 | Mount | A61G 15/125 5/638 |
| 2016/0151222 | A1 * | 6/2016 | Pedro | A61M 16/01 128/845 |
| 2016/0228326 | A1 * | 8/2016 | Lurie | A61G 13/129 |
| 2016/0317371 | A1 * | 11/2016 | Wooden | A61G 13/1235 |
| 2016/0374630 | A1 * | 12/2016 | Smith | A61B 6/501 378/209 |
| 2019/0059852 | A1 * | 2/2019 | Zwierstra | A61B 5/026 |

FOREIGN PATENT DOCUMENTS

| | | |
|---|---|---|
| JP | 40420334 A | 1/1992 |
| JP | H07289544 A | 11/1995 |
| JP | H0975333 A | 3/1997 |

OTHER PUBLICATIONS

CIVCO Radiotherapy, "Variable Axis Baseplate, Posifix®," www.civcort.com/ro/head-neck/posifixbaseplates/Posifix-Variable-Axis-Baseplate.htm, Access date Nov. 9, 2017.

* cited by examiner

ADJUSTABLE COMPUTED TOMOGRAPHY HEAD FIXATOR FOR NEUROLOGICAL SCANS

CROSS-REFERENCE TO RELATED APPLICATIONS

The present application claims priority to U.S. Provisional Application 62/657,579 entitled "Adjustable Computed Tomography Head Fixator for Neurological Scans" and filed on Apr. 13, 2018.

BACKGROUND

Computed Tomography (CT) is an effective medical imaging tool due to its ability to capture diagnostic quality images of bone and soft tissue. A CT scan uses a rotating beam of x-rays aimed at a patient, which produce a signal in a row of detectors that lie 180 degrees from the outgoing radiation beam. More specifically, the patient lays on a bed that glides them through the gantry of the CT scanner; as they move through the machine, the x-ray beams revolve around them so that all required anatomy is exposed to radiation and corresponding signals are detected. A cross-sectional image is reconstructed from these signals by a computer.

Children with craniofacial anomalies often require pre- and post-operative CT scans and children with traumatic brain injuries or hydrocephalus often require multiple CT scans. However, it is known that pediatric patients are more susceptible CT radiation. Furthermore, it is generally accepted, though controversial, that cumulative effects of radiation dose such as that delivered from repeated head CT scans increases the risk of developing cataracts and cancer by three to four times.

In older model CT scanners, which have a single or up to sixteen rows of detectors, the gantry can tilt to an angle. Thus, for head CT scans, the gantry can be tilted to eliminate the thyroid gland and/or the lenses of the eyes from the scanner field of view while still permitting imaging of the desired anatomy. Advancements in CT scanner technology, however, have increased the number of detector rows up to 320 in new models. This increases the weight and rotational geometry of the scanner such that it is infeasible for the gantry to tilt and maintain the required rotation speed. In particular, this change in angular momentum in newer scanners would result in the destruction of the CT scanner and be unsafe for patients. Therefore, newer CT models do not allow for gantry tilt.

When using newer CT models, instead of tilting the gantry, the patient's head angle must be adjusted into flexion by tilting the chin to the chest, thus aligning the orbitomeatal line to be parallel with the CT scanner gantry and eliminating the lens of the eyes from direct radiation exposure. Furthermore, by changing the head angle to an extended position, the entire head and face can be scanned while eliminating the thyroid gland from the scan field of view. Although changing the head angle can help eliminate unnecessary radiation to certain anatomy, currently used head-holders for CT scanners are not adjustable. Thus, only a very limited degree of head positioning is achievable (e.g., with a stack of sheets, a pillow, or towels to prop the patient up). As a result, radiation exposure to sensitive tissues such as the lens of the eye and the thyroid gland regularly occurs.

Therefore, there is a need for an adjustable head-holder or fixator capable of securely positioning a patient's head at an angle in which a CT scan can be performed while eliminating or including particular anatomy. Such an adjustable head-holder is needed for mitigation of radiation dose—an issue applicable to both child and adult CT imaging. Such a holder would also optimize image orientation for improving presentation of anatomy and thereby increasing diagnostic confidence.

SUMMARY

Embodiments of the present invention provide a device that orients a patient's head into an idealized position so the desired anatomy can be imaged and radiosensitive organs are excluded from the scanner field of view. In doing so, the present device can decrease scan time and reduce total radiation dose.

DETAILED DESCRIPTION

Figure 1:
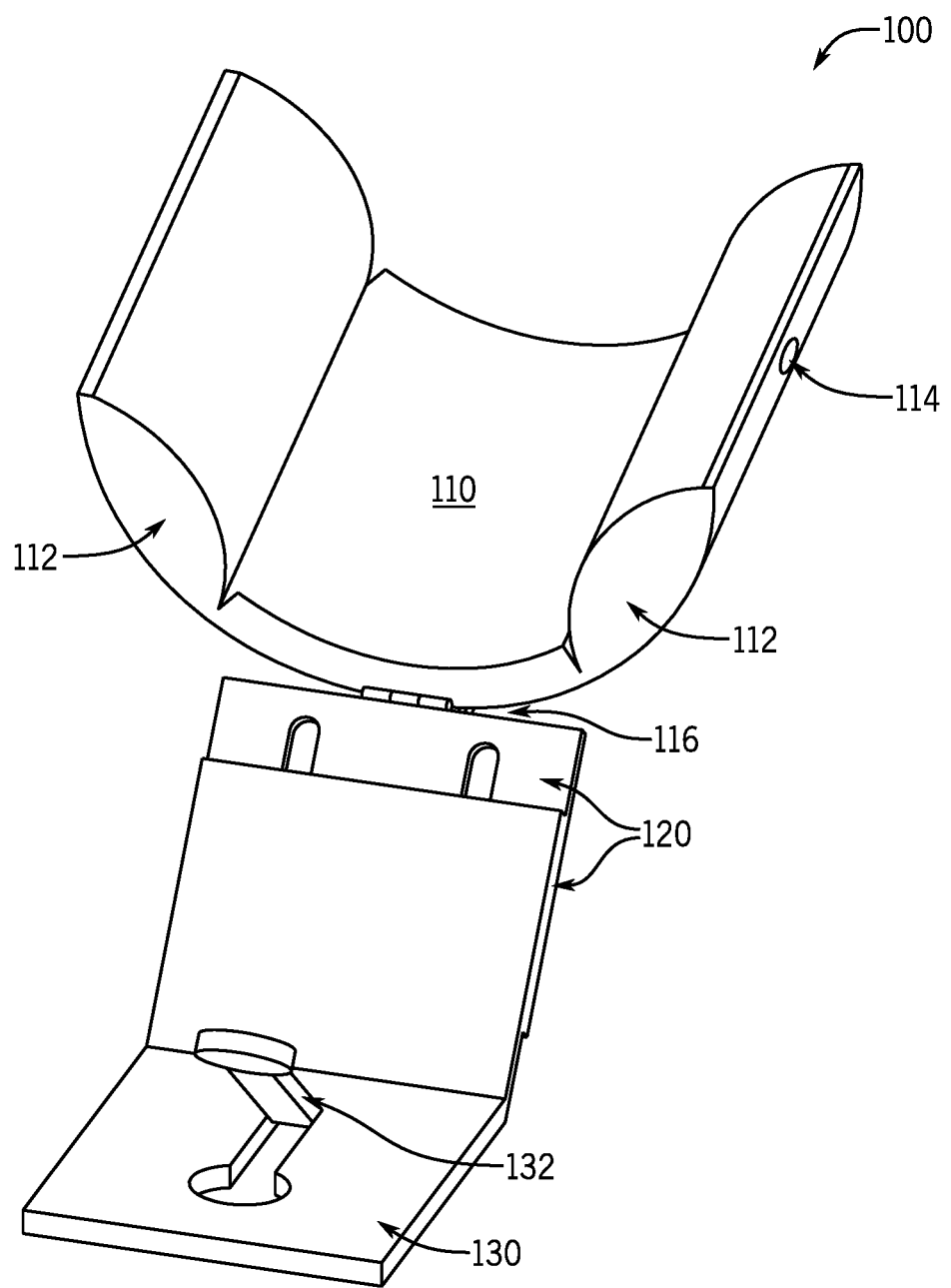
FIG. 1 is a front perspective view of a head fixator device according to one embodiment of the invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention.

In newer models of CT scanners, unlike older CT scanner models, the gantry does not tilt. Due to this, CT technologists now often scan, for example, the entire head and neck of the patient when a craniofacial defect is suspected. Or, in another example, CT technologists scan the entire brain and eyes if the patient has a neurological disorder. Since the thyroid gland and lenses of the eyes are sensitive to ionized radiation, there is potential risk to the patient. This risk of cancer induction or cataract formation is believed to be especially important in pediatrics as children are believed to be more sensitive to effects of radiation than are adults.

Therefore, positioning the head at an angle in order to eliminate the thyroid gland or the lenses of the eyes from the direct radiation beam, depending on the indication for the CT scan, is of paramount importance. For example, in craniofacial CT examinations the entire head, from the vertex (top of the head) to the tip of the chin must be scanned. In a patient lying on their back on a CT bed with the head in a neutral position, the chin is typically tipped below the level of the thyroid gland. Therefore, the thyroid gland is included in the scan field of view. By adjusting the angle of the head into an extended position, the tip of the chin is aligned vertically with the occiput or the posterior, inferior margin of the head, and the thyroid gland is not included into the scan field of view and is not directly radiated. In other words, by adjusting the angle of the head into the extended position, the lower mandible (i.e., bottom jaw) and the occiput or the posterior, inferior margin of the head can form two imaginary lines that run parallel with the plane of the gantry. An additional benefit of an extended head position is that the length of the scan required to include the required anatomy is reduced. Consequently, total radiation dose is reduced. Though the lenses of the eyes are included in the scan field of view, imaging of this anatomy is diagnostically important as the orbits may be abnormal in children with cranial anomalies.

Similar benefits of specific head position occur when a CT scan of the brain is performed. A brain or head CT requires that imaging of the brain, but not the face, be included in the final images. Eliminating the lenses of the eyes from the scan field of view can help reduce the risk of cataract formation caused by radiation. To do so, the head can be placed in a flexed position with the chin tipped toward the sternum, allowing the orbitomeatal line (e.g., anatomically the roof of the orbit and the external auditory canal) to be vertical, aligned with the CT scanner gantry. The scan field of view is thereby shortened to include the brain only and not the face. The lenses of the eyes and the thyroid gland are not included in the scan field of view.

In light of the above, embodiments of the present invention provide a head fixator device that allows a CT technologist to readily, efficiently, and accurately position the patient's head in a consistent manner. The present invention can be coupled to a CT scanner bed so that the patient's head may be positioned optimally for the specific examination of interest, reducing unnecessary radiation exposure to certain areas of the body. The present device is applicable to brain/head CT scanning for patients of all ages, including those with craniofacial anomalies, brain trauma, hydrocephalus, or any other neurological defect that may require a CT scan. In some embodiments, the present device may be applicable to patients of all ages, patients two months or older, or patients in another age group. The device can provide for optimal patient positioning, patient comfort, reduction of potential motion artifact, optimizing head position for improved CT image quality and diagnostic confidence, and radiation dose reduction, especially to radiosensitive tissues such as the thyroid gland and the lenses of the eyes.

Accordingly, it is an object of the invention to provide a mechanism for brain/head CT scans so that the angle of the head can be adjusted. It is another object of the invention to decrease the time it takes to complete a scan of the patient's brain/head. It is a further object of the invention to decrease the radiation dose that the patient is exposed to (or absorbs) during a brain/head CT scan. It is yet another object of the invention to remove the opportunity for head motion during brain/head CT, which may lead to artifacts or image degradation. It is another object of the invention that the device is compatible with various CT scanners made by different CT manufacturers.

Figure 2:
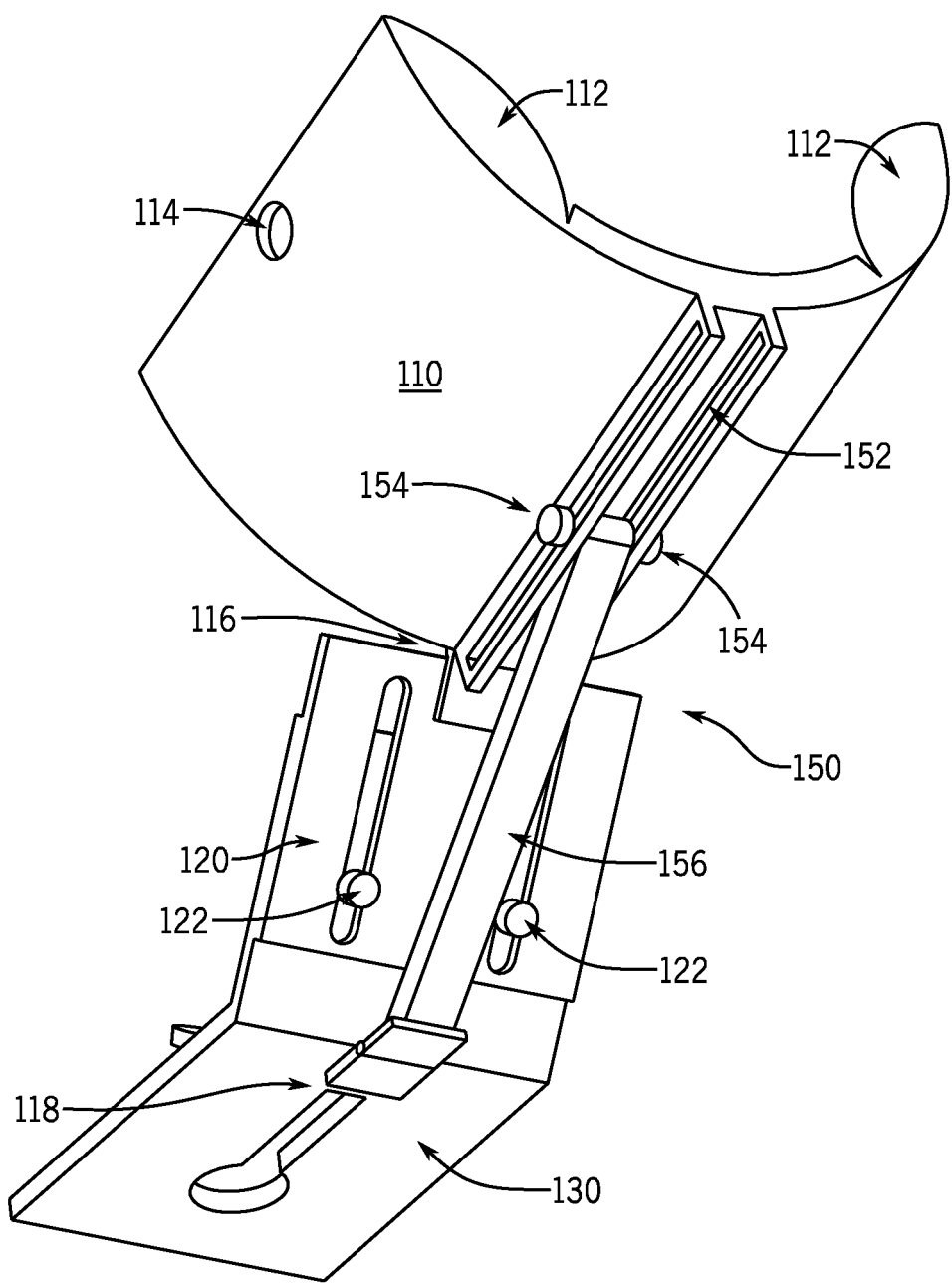
FIG. 2 is a rear perspective view of the device of FIG. 1.

FIGS. 1 and 2 illustrate parts of the device, according to one embodiment. As shown in FIG. 1, the head-holder device 100 includes an insertion tab 130 (i.e., a base), a hemicylindrical headrest 110 including adjustable, inflatable chambers 112, a neckpiece 120 including an apparatus to adjust the height of the neck (shown in FIG. 2), and an apparatus to adjust the angle of the headrest relative to the neckpiece 120 (shown in FIG. 2). In some embodiments, the head-holder device 100 can be made out of carbon fiber. The head-holder device 100 can be coupled to a bed of a CT scanner via the insertion tab 130 and insertion tab lock 132 and, as further described below, can be configured to ensure the patient is resting comfortably on the bed at an appropriate head angle.

Figure 3:
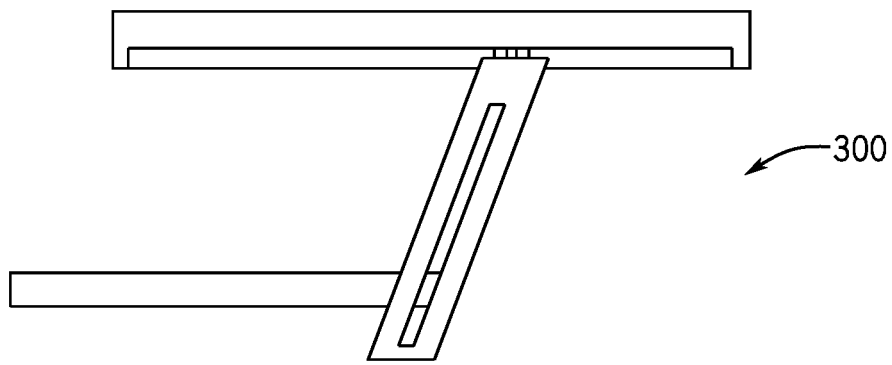
FIG. 3 is a series of schematic views of an angle adjustment mechanism of a head fixator device.

Generally, the head-holder device 100 includes an adjustable track that is moved by a rotating set of gears. More specifically, as shown in FIG. 2, the apparatus to adjust the angle of the headrest includes a sliding track 152 coupled to a bottom of the hemicylindrical headrest 110, an angle arm 156 coupled to the insertion tab 130 with a hinge 118 and adjustable along the sliding track 152, and fixator knobs 154 to fix a position of the angle arm 156 on the sliding track 152. FIG. 3 also illustrates an example scissors splint mechanism 300 that can be used in some embodiments for the head angle adjustment mechanism.

The sliding track 152 will keep the angle arm 156 on the right path as well as play a role in securing the position of the headrest 110. More specifically, by sliding the angle arm 156 along a stationary track 152, a patient's head position will be readily adjusted as the angle of the head-holder changes. In one embodiment, the angle can be adjusted between about −30 degrees and +30 degrees (e.g., from horizontal). The angle arm 156 can be fixed into position by tightening fixator knobs 154 on each side of the track. For example, when the fixator knobs 154 on the side of the track 152 are tightened the position of the headrest 110 will be fixed, and when the knobs are loosened the headrest 110 will be allowed to be adjusted (e.g., moveable along the track 152).

Thus, by securely positioning the head at the proper angle, the ultimate goal of avoiding direct radiation to, for example, the thyroid gland or the lenses of the eyes, ensuring a comfortable and immobile patient, and decreasing the scan time and radiation dose is achieved. More specifically, the angle allows the head to be positioned in a flexed position (chin to the chest) or in an extended position (chin up in the air) so that radiosensitive tissues may be excluded from the scan field of view, while relevant anatomy is imaged.

Figure 4:
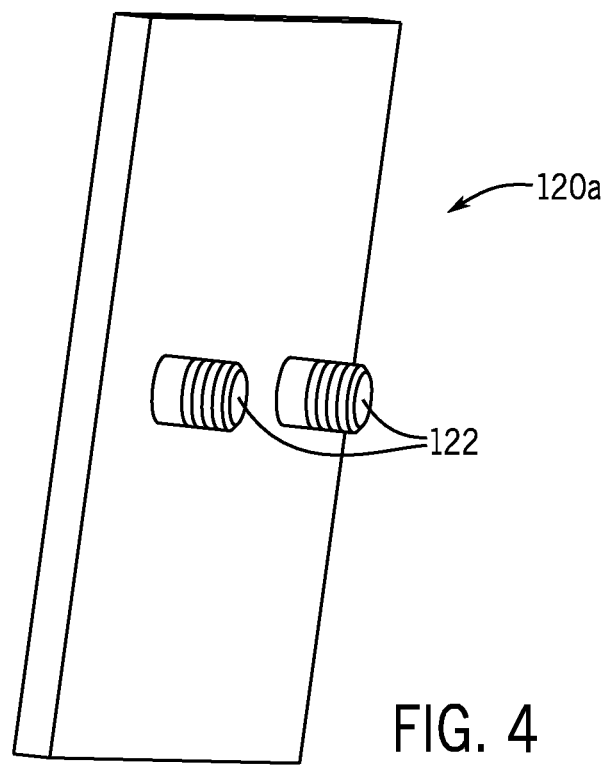
FIG. 4 is a rear perspective view of a portion of a neckpiece of the device of FIG. 1.
Figure 5:
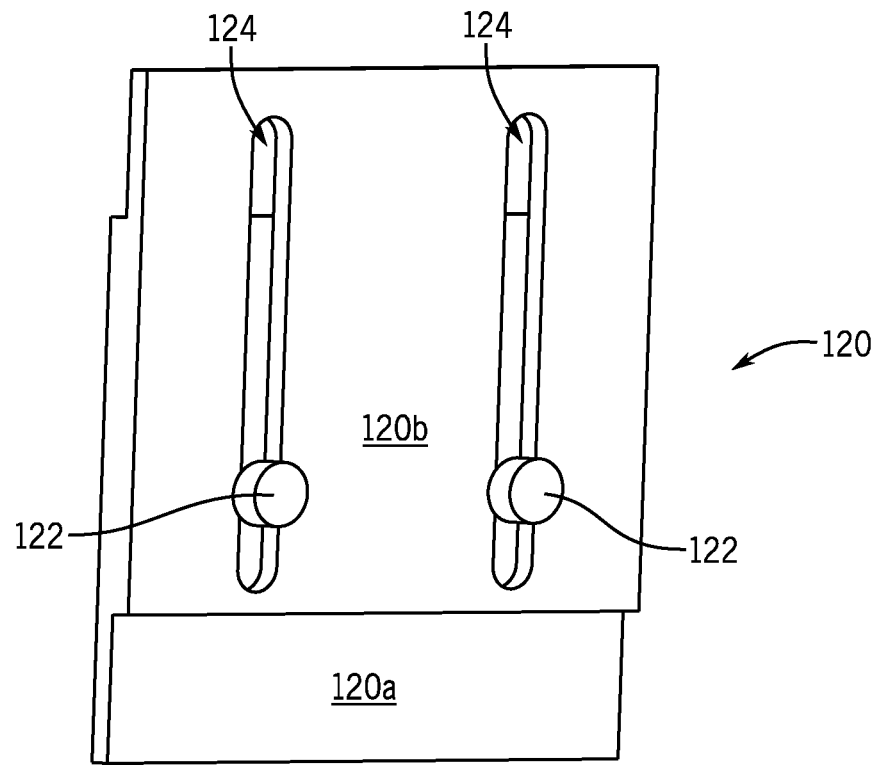
FIG. 5 is a rear view of a neckpiece of the device of FIG. 1 in a first position.
Figure 6:
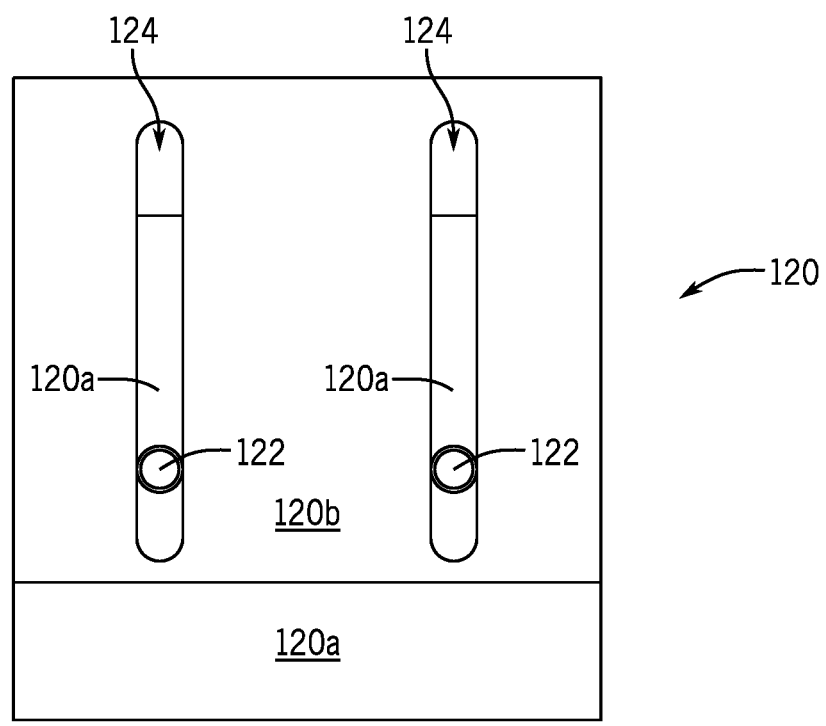
FIG. 6 is a rear perspective view of a neckpiece of the device of FIG. 1 in the first position.
Figure 7:
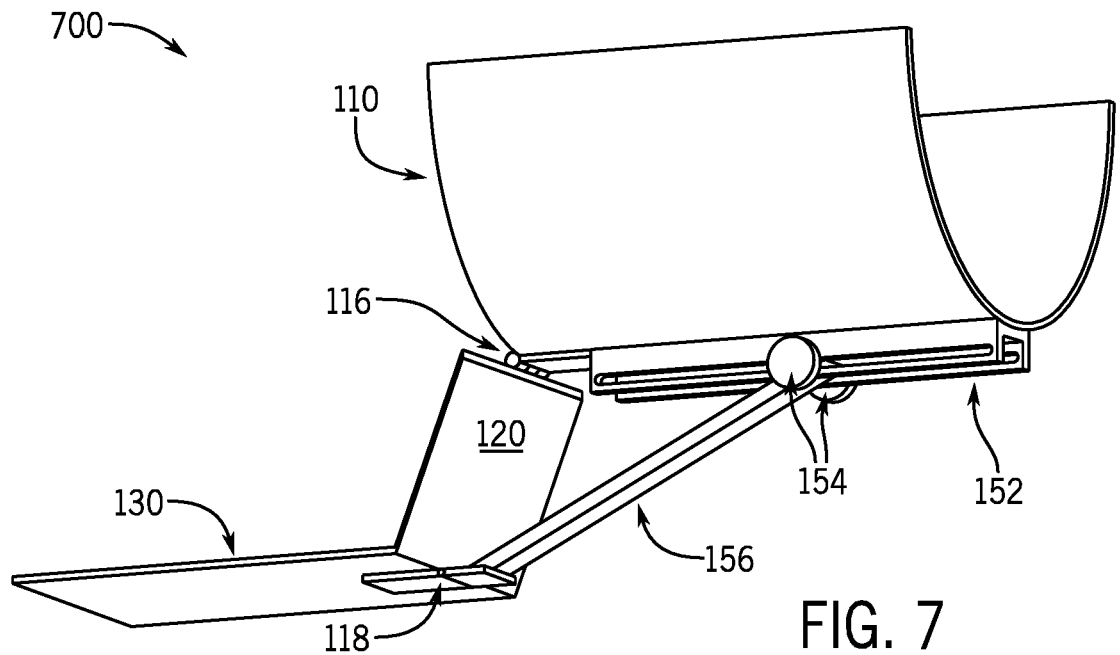
FIG. 7 is a rear perspective view of a head fixator device according to one embodiment of the invention.
Figure 8:
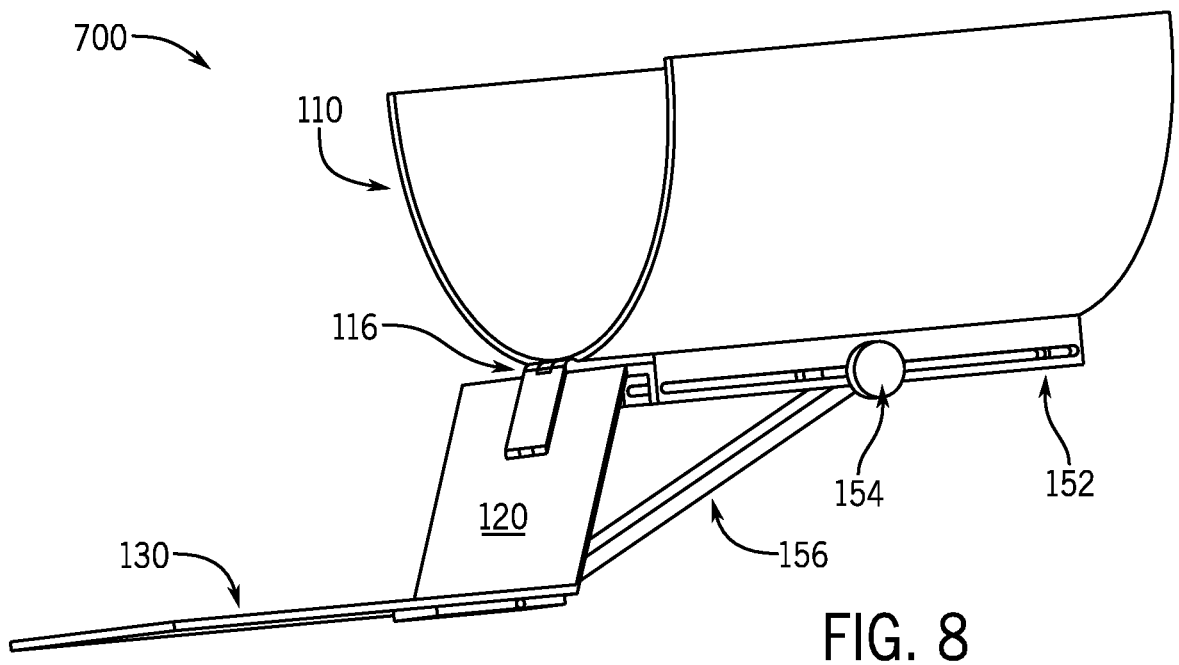
FIG. 8 is a front perspective view of the device of FIG. 7.
Figure 9:
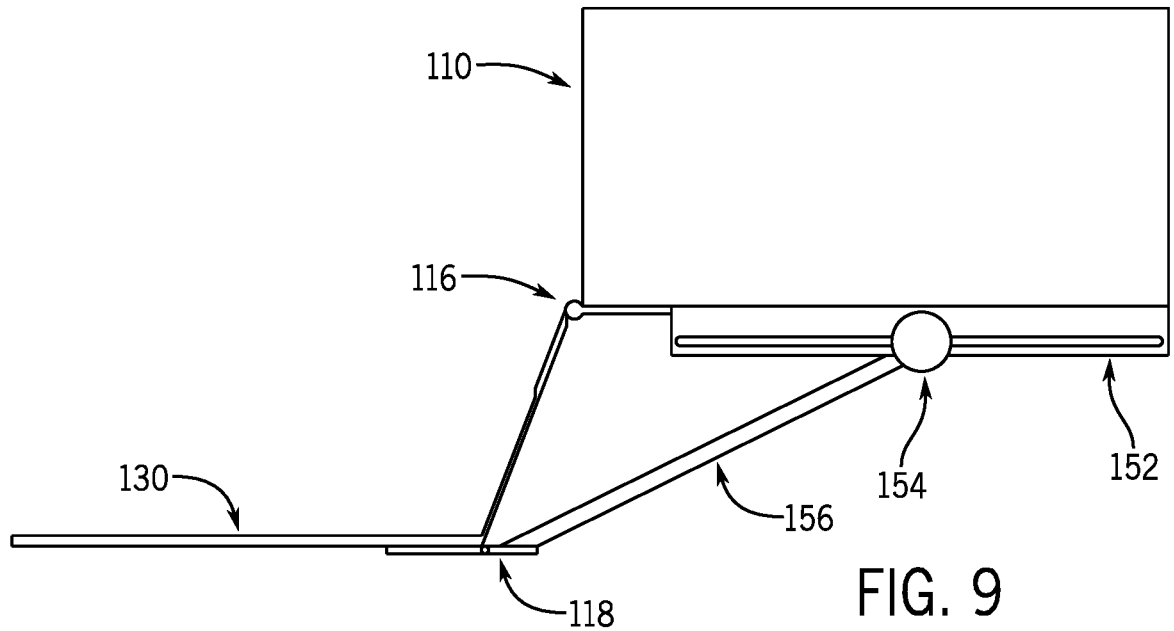
FIG. 9 is a side view of the device of FIG. 7.

Also, the same procedure applies to the adjustable neck length of the neckpiece 120. As shown in FIGS. 4-6, the neckpiece 120 includes two pieces 120a, 120b which slide relative to each other. The pieces 120a, 120b are fixed at a specific position by tightening knobs 122 along slots 124 in piece 120b. Adjusting the neckpiece 120 will change the elevation and angle of the headrest 110 at which the head is being held. Accordingly, the head-holder device 100 and, more specifically, the neckpiece 120, provides for adjustable neck length, which allows the head-holder device 100 to be adjusted for patients of all sizes, from newborn to a large adult, and for CT beds from all manufacturers. Alternatively, in some embodiments such as example embodiment 700, as shown in FIGS. 7-9, the device may only include the adjustable angle mechanism 150 and the length of the neckpiece 120 is not adjustable, although still hinged (see hinge 116) at the headrest 110 and insertion tab 130 as shown. Note that similar parts of embodiment 700 are labeled with the same part numbers as analogous parts of head-holder device 100.

In some embodiments, adjustable, inflatable chambers 112 (shown in FIGS. 1-2) on the headrest 110 further permit optimized head position and limit potential motion artifact. In order to use the adjustable, inflatable chambers 112 on the headrest 110, the CT technologist can use a pump apparatus coupled to an inflation port 114. The adjustable, inflatable chambers 112 also provide for a universal headrest 110 for patients of all sizes (e.g., where smaller patients require additional inflation to immobilize the head, while larger patients may require less inflation). The design allows for ease of use by CT technologists, radiology nurses, and others involved in the CT scan process such as respiratory technologists and anesthesiologists.

Operation of the device is as follows. First, lay the patient down onto the CT bed and gently place their head into the hemicylindrical headrest 110. Next use the knobs 122 to secure the headrest 110 in the specific angle (i.e., by adjusting the angle arm 156 along the track 152) and/or height (i.e., by adjusting the neckpiece 120 components). Finally inflate the chambers 112 on the headrest 110 to a comfortable level to aid the patient in lying still. Begin scanning.

Accordingly, this head-holder device 100 can decrease the time it takes to scan a patient's head or brain. It will also enable the radiation dose given to the patients during the scan to be reduced. The part of the head-holder device 100 that makes it unique is the apparatus that allows the headrest 110 to move up and down which allows the angle of the head to change. Its ease of use is also a unique characteristic since it is so easy to use that anyone who has hands is able to use it.

Additionally, in some situations, it may be necessary to intubate a patient while the patient is on the scanner bed. As such, various embodiments provide a quick adjustment mechanism to position the patient's head at an optimal angle for intubation.

Figure 10:
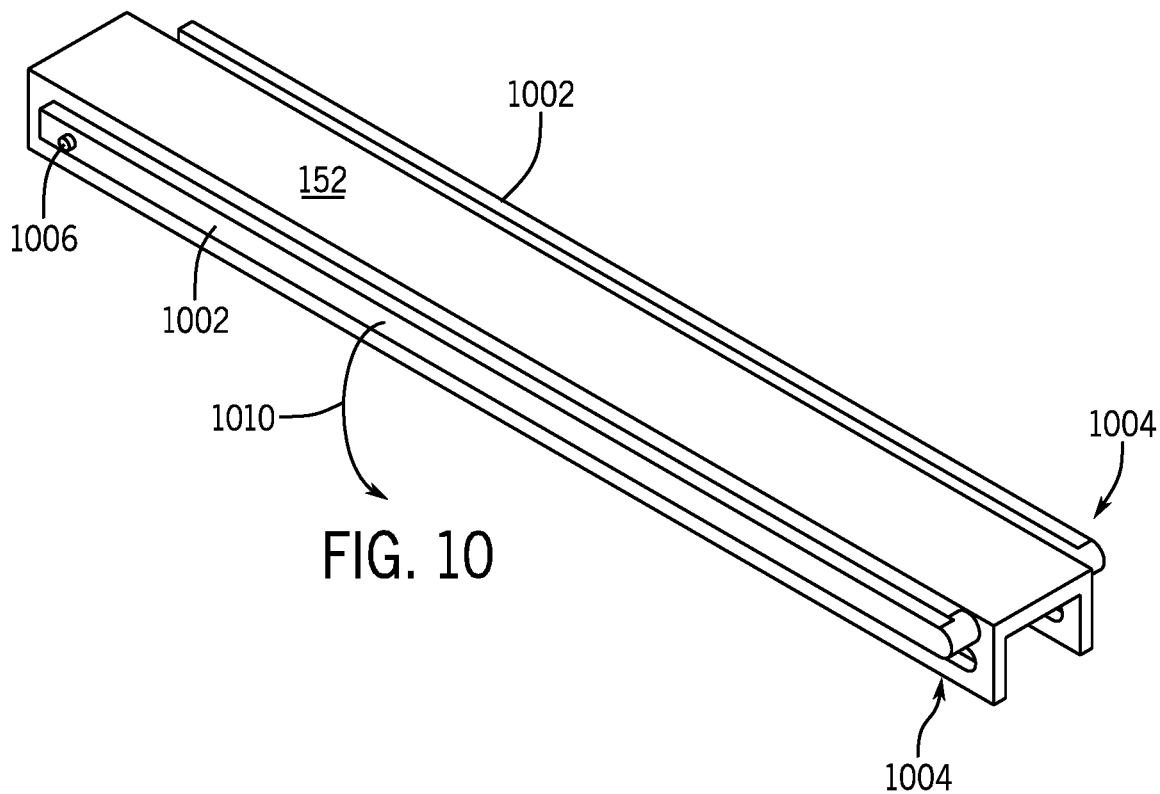
FIG. 10 is a perspective view of an intubation mechanism, according to one embodiment, for use with the devices of FIGS. 1 and 7.

According to one embodiment, as shown in FIG. 10, the device can include intubation bars 1002 attached to the sides of the sliding track 152 by a hinge 1004 on one end and a pullpin 1006 on the other end. The intubation bars 1002 are held adjacent to the sliding track 152, in the position shown in FIG. 10, by the pullpin 1006. The intubation bars 1002 have the ability to rotate (as illustrated by the arrow 1010) once the pullpin 1006 is pulled out and no longer obstructing the rotational pathway of the intubation bars 1002.

These intubation bars 1002 have a locking mechanism inside the circular hinge 1004 that will stop it from rotating past a predetermined point. As such, when the pullpin 1006 is pulled out, the intubation bars 1002 will rotate a predetermined degree of rotation until locked by the hinge 1004. At this predetermined degree, the intubation bars 1002 contact the CT bed to hold the headrest 110 at an optimal angle for intubating the patient. Thus, when a patient needs to be intubated, a technician can loosen the fixator knobs 154 (thus allowing free movement of the angle arm 156 along the sliding track 152), pull out the pullpin 1006, and move the headrest 110 until the intubation bars 1002 rotate their full degree of rotation and contact the CT bed. At that position, the patient is at an optimal angle for intubation.

Figure 11:
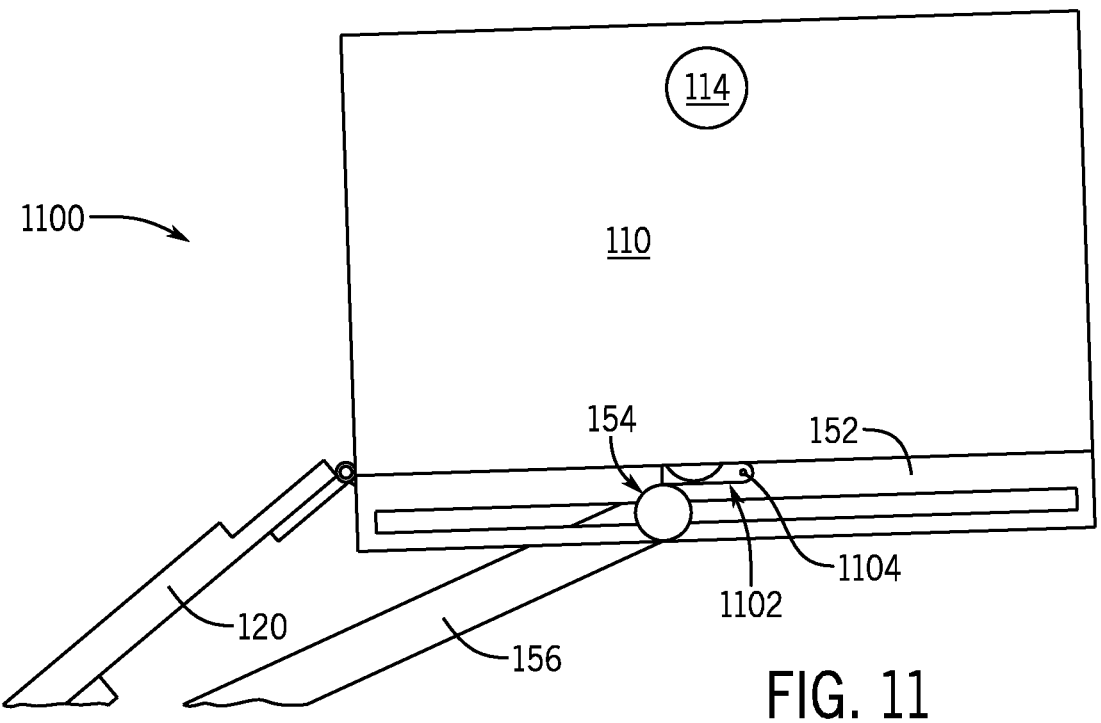
FIG. 11 is a side view of a head fixator device with an intubation mechanism, according to one embodiment, in a first position.
Figure 12:
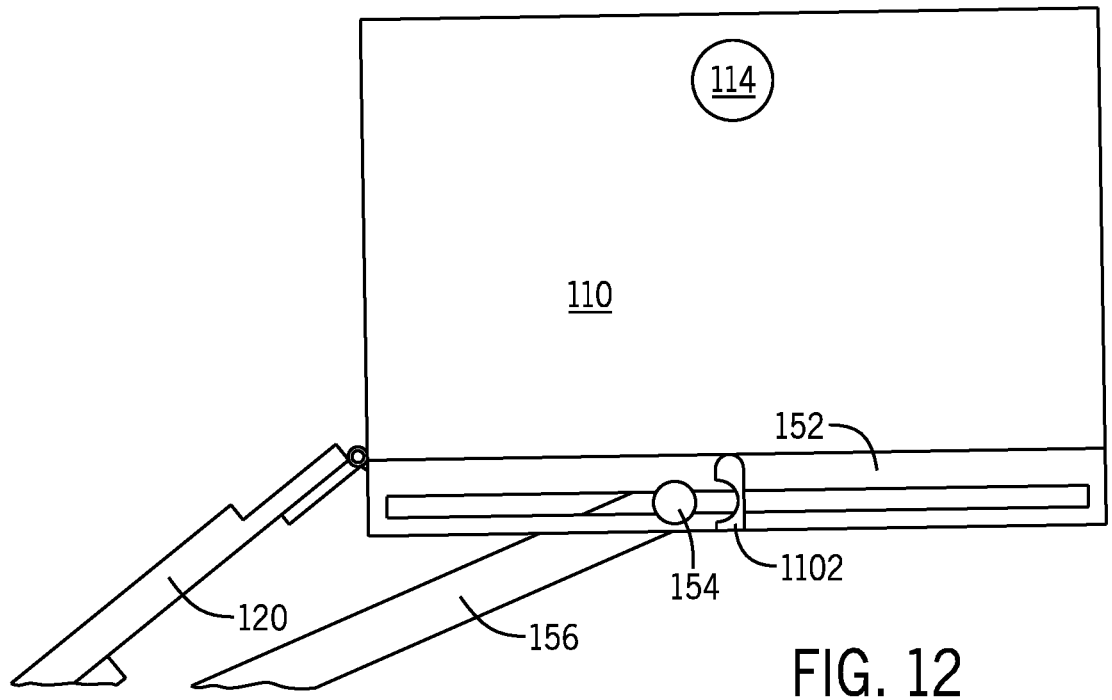
FIG. 12 is a side view of the head fixator device with the intubation mechanism in a second position.

According to another embodiment 1100, as shown in FIGS. 11 and 12, the device can include an intubation cradle 1102 attached to the sides of the sliding track 152 by a hinge 1104 on one end and a pullpin (not separately shown) on the other end. Similar to the intubation bars described above, the intubation cradle 1102 is held in place in a first position (e.g., on the sliding track 152 above the fixator knobs 154, as shown in FIG. 11) by the pullpin. Note that the intubation cradle 1102 is separated from the fixator knob 154 by a small space which is not visible due to the scale of the drawing. Thus, the intubation cradle 1102 can rotate downward (e.g., counterclockwise from the position shown in FIG. 11) when the pullpin is pulled out toward a second position, as shown in FIG. 12.

The intubation cradle 1102 can include a locking mechanism inside the hinge 1104 that will stop it from rotating past a predetermined point (such as, further example, 90 degrees, as shown in FIG. 12). As such, when the pullpin is pulled out, the cradle will rotate a predetermined degree of rotation until locked by the hinge. The intubation cradle 1102 can be positioned along the track 152 so that, when rotated to this predetermined degree, the fixator knobs 154 can be adjusted to rest against the intubation cradle 1102 (i.e., the circular portion of the cradle) to hold the headrest 110 at an optimal angle for intubating the patient. Thus, when a patient needs to be intubated, a technician can loosen the fixator knobs 154 (thus allowing free movement of the angle arm 156 along the sliding track 152), pull out the pullpin, and move the headrest 110 until the fixator knobs 154 rest against the intubation cradle 1102. At that position, the patient is at an optimal angle for intubation.

Figure 13:
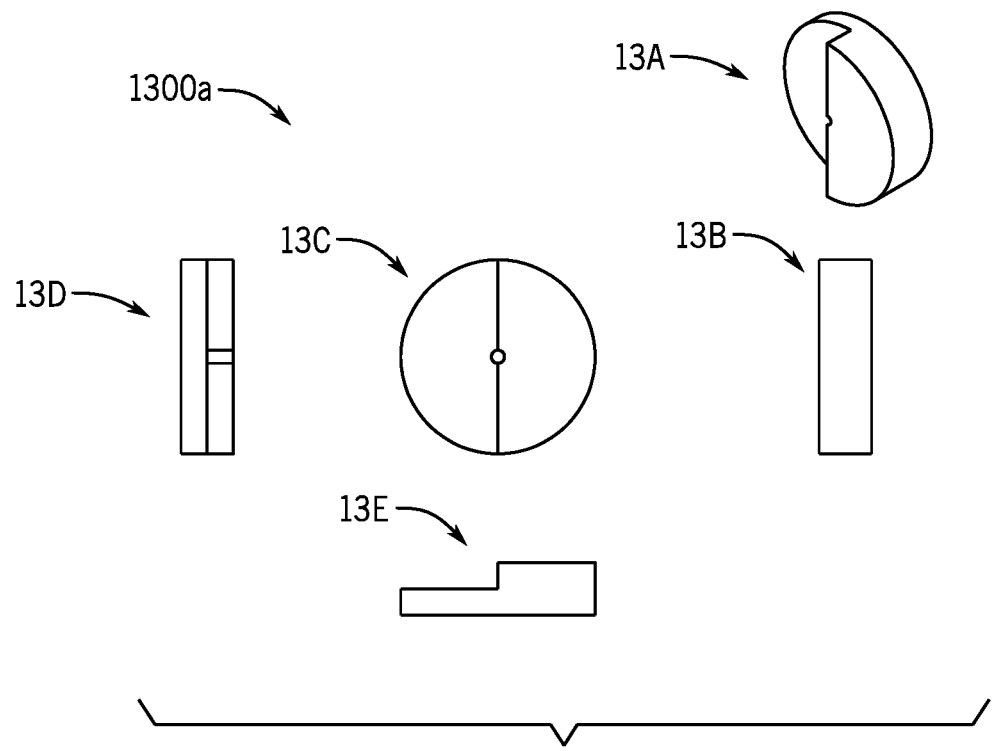
FIG. 13 is a series of views of a first half of a hinge mechanism for use with the intubation mechanisms of FIGS. 10-12.
Figure 14:
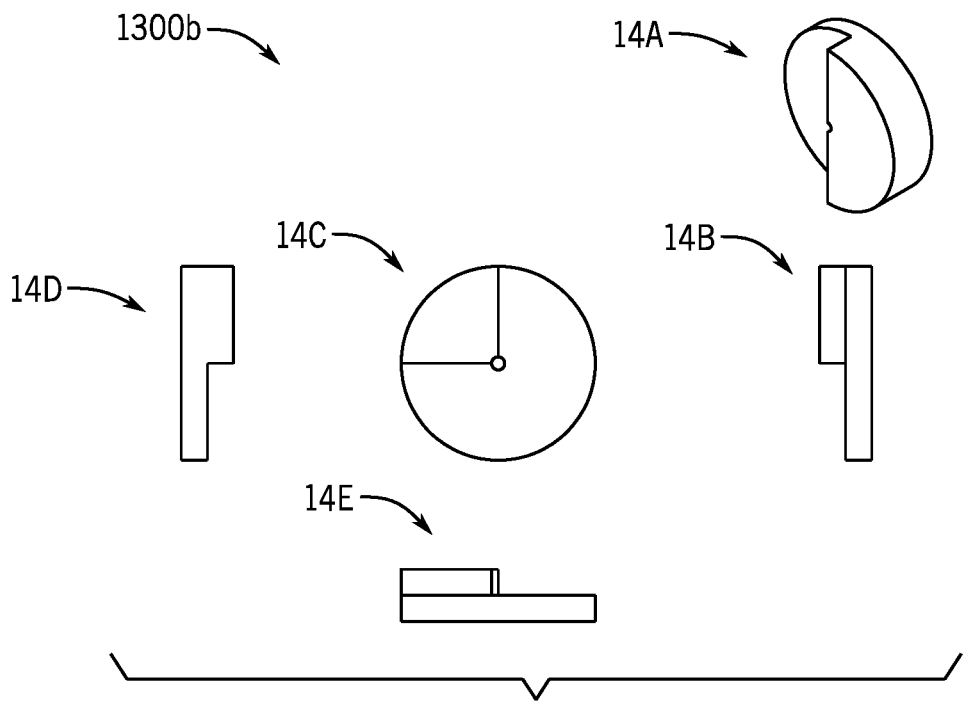
FIG. 14 is a series of view of a second half of the hinge mechanism for use with the intubation mechanisms of FIGS. 10-12.
Figure 15:
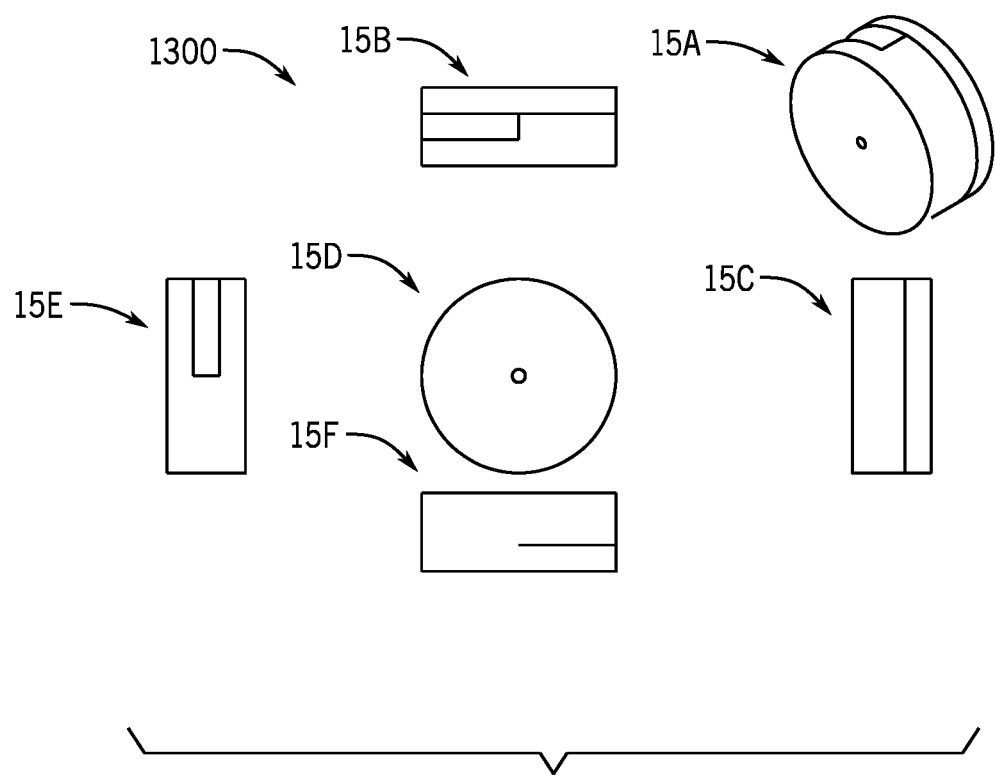
FIG. 15 is a series of views of the assembled hinge mechanism for use with the intubation mechanisms of FIGS. 10-12.

FIGS. 13-15 illustrate an example hinge 1300 having an outside half 1300a and inside half 1300b for use with the intubation bars (i.e., hinge 1004 shown in FIG. 10) or the intubation cradle (i.e., hinge 1104 shown in FIG. 11) described above. FIG. 13 shows five views 13A-E of an inside half of the hinge and stopping mechanism. This part will be secured along the outside wall of the slide track 152. FIG. 14 shows five views 14A-E of the outside part of a hinge and stopping mechanism. The quarter wedge will ensure that the intubation cradle can only rotate down 90 degrees because it will be stopped by the inside part of the hinge and stopping mechanism (as shown in FIG. 13). FIG. 15 shows six views 15A-F of the hinge and stopping mechanism assembled.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein. Various features and advantages of the invention are set forth in the following claims.

We claim:

1. A head fixator for positioning a patient's head during imaging, comprising:
   a headrest dimensioned to cradle a patient's head;
   a neckpiece coupled to the headrest by a first hinge at a first end of the neckpiece;
   a track coupled to a bottom surface of the headrest;
   an adjustable angle arm coupled to the track at a first end of the angle arm and coupled by a second hinge to the neckpiece at a second end of the angle arm, the first end of the angle arm configured to slide within the track, a position of the angle arm within the track determining an angle between the headrest and the neckpiece;
   one or more fixator fasteners coupled to the first end of the angle arm and passing through one or more slots in the track, wherein:
      when the fixator fasteners do not securely couple the first end of the angle arm to the track, the angle arm is configured to slide freely within the track, allowing the angle between the headrest and the neckpiece to be adjusted to a desired angle, and
      when the angle between the headrest and the neckpiece is the desired angle and the fixator fasteners securely couple the first end of the angle arm to the track, the angle arm is configured to maintain the desired angle between the headrest and the neckpiece; and
   one or more intubation bars coupled to corresponding sides of the track, each intubation bar coupled to the corresponding side of the track at a first end of the intubation bar by at least a third hinge and dimensioned to be coupled to the corresponding side of that track at a second end of that intubation bar by a first pullpin dimensioned to couple to the track through a second end of that intubation bar,
      wherein when the fixator fasteners do not securely couple to the first end of the angle arm to the track and the first pullpin of each intubation bar is removed:
         that intubation bar is configured to pivot about its first end, and
         the second end of that intubation is configured to rest on the patient bed beneath the track, maintaining a predefined angle between the headrest and the neckpiece, the predefined angle being desirable for intubating a patient; and
   a base coupled to a second end of the neckpiece, the base dimensioned to form an insertion tab configured to fasten the head fixator to a patient bed.

2. The head fixator of claim 1, wherein the neckpiece comprises a first neckpiece section and a second neckpiece section; and
   wherein the first neckpiece section and the second neckpiece section are configured to slide relative to one another along a line extending between the base and the headrest, a position of the first neckpiece section relative to the second neckpiece section defining a length of the neckpiece.

3. The head fixator of claim 2:
   wherein the first neckpiece section is dimensioned with one or more slots and the second neckpiece is dimensioned to couple to one or more neck fasteners passing through the one or more slots;
   wherein when the one or more neck fasteners do not securely fasten the first neckpiece section to the second neckpiece section, the length of the neckpiece is adjustable by translating the first neckpiece section relative to the second neckpiece section; and
   wherein when the length of the neckpiece is a desired neck length and the one or more neck fasteners securely fasten the first neckpiece section to the second neckpiece section, the length of the neckpiece is fixed as the desired neck length.

4. The head fixator of claim 1, further comprising:
   one or more intubation cradles coupled to corresponding sides of the track, each intubation cradle coupled to the corresponding side of the track at a first end of the intubation bar by at least a third hinge and dimensioned to be coupled to the corresponding side of that track at a second end of that intubation bar by a second pullpin dimensioned to couple to the track through a second end of that intubation bar;
   wherein each intubation cradle is provided with a recess in a face of that intubation cradle, the recess dimensioned to receive one of the fixator fasteners, the face provided along an edge of the intubation bar oriented perpendicular to a direction of translation of the angle arm within the track; and
   wherein, when the fixator fasteners do not securely couple the first end of the angle arm to the track and the second pullpin of each intubation cradle is removed:
      that intubation cradle is configured to pivot about its first end,
      the second end of that intubation cradle is configured to rotate such that the intubation cradle remains in a fixed position, presenting the recess of that intubation cradle to a fixator fastener adjacent to that intubation cradle, and
      when the angle bar is allowed to translate within the rack and the one or more fixator fasteners are positioned forward of the one or more intubation cradles, the one or more intubation cradles are configured to maintain a predefined angle between the headrest and the neckpiece, the predefined angle being desirable for intubating a patient.

5. The head fixator of claim 1, further comprising one or more flexible chambers disposed within corresponding sidewalls of the headrest;
   wherein the flexible chambers are inflatable and deflatable to adjust an inner dimension of the headrest to the patient's head.

6. A system for positioning a patient during imaging, comprising:
- a headrest dimensioned to cradle a patient's head;
- a neckpiece coupled to the headrest by a first hinge at a first end of the neckpiece;
- a track coupled to a bottom surface of the headrest;
- an adjustable angle arm coupled to the track at a first end of the angle arm and coupled by a second hinge to the neckpiece at a second end of the angle arm, the first end of the angle arm configured to slide within the track, a position of the angle arm within the track determining an angle between the headrest and the neckpiece;
- one or more fixator fasteners coupled to the first end of the angle arm and passing through one or more slots in the track, wherein:
  - when the fixator fasteners do not securely couple the first end of the angle arm to the track, the angle arm is configured to slide freely within the track, allowing the angle between the headrest and the neckpiece to be adjusted to a desired angle, and
  - when the angle between the headrest and the neckpiece is the desired angle and the fixator fasteners securely couple the first end of the angle arm to the track, the angle arm is configured to maintain the desired angle between the headrest and the neckpiece;
- one or more intubation cradles coupled to corresponding sides of the track, each intubation cradle coupled to the corresponding side of the track at a first end of the intubation bar by at least a third hinge and dimensioned to be coupled to the corresponding side of that track at a second end of that intubation bar by a first pullpin dimensioned to couple to the track through a second end of that intubation bar, wherein each intubation cradle is provided with a recess in a face of that intubation cradle, the recess dimensioned to receive one of the fixator fasteners:
  - when the fixator fasteners do not securely couple the first end of the angle arm to the track and the first pullpin of each intubation cradle is removed:
    - that intubation cradle is configured to pivot about its first end so that the face provided along an edge of the intubation bar is oriented perpendicular to a direction of translation of the angle arm within the track,
    - the second end of that intubation cradle is configured to rotate such that that intubation cradle remains in a fixed position, presenting the recess of that intubation cradle to a fixator fastener adjacent to that intubation cradle, and
  - when the angle bar is allowed to translate within the rack and the one or more fixator fasteners are positioned forward of the one or more intubation cradles, the one or more intubation cradles are configured to maintain a predefined angle between the headrest and the neckpiece, the predefined angle being desirable for intubating a patient and
- a base coupled to a second end of the neckpiece, the base dimensioned to form an insertion tab configured to fasten to a first end of a patient bed.

7. The system of claim 6, wherein the neckpiece comprises a first neckpiece section and a second neckpiece section; and
- wherein the first neckpiece section and the second neckpiece section are configured to slide relative to one another along a line extending between the base and the headrest, a position of the first neckpiece section relative to the second neckpiece section defining a length of the neckpiece.

8. The system of claim 7:
- wherein the first neckpiece section is dimensioned with one or more slots and the second neckpiece is dimensioned to couple to one or more neck fasteners passing through the one or more slots;
- wherein when the one or more neck fasteners do not securely fasten the first neckpiece section to the second neckpiece section, the length of the neckpiece is adjustable by translating the first neckpiece section relative to the second neckpiece section; and
- wherein when the length of the neckpiece is a desired neck length and the one or more neck fasteners securely fasten the first neckpiece section to the second neckpiece section, the length of the neckpiece is fixed as the desired neck length.

9. The system of claim 6, further comprising:
- one or more intubation bars coupled to corresponding sides of the track, each intubation bar coupled to the corresponding side of the track at a first end of the intubation bar by at least a third hinge and dimensioned to be coupled to the corresponding side of that track at a second end of that intubation bar by a second pullpin dimensioned to couple to the track through a second end of that intubation bar; and
- wherein, when the fixator fasteners do not securely couple to the first end of the angle arm to the track and the second pullpin of each intubation bar is removed:
  - that intubation bar is configured to pivot about its first end; and
  - the second end of that intubation is configured to rest on the patient bed beneath the track, maintaining a predefined angle between the headrest and the neckpiece, the predefined angle being desirable for intubating a patient.

10. The head fixator of claim 6, further comprising one or more flexible chambers disposed within corresponding sidewalls of the headrest;
- wherein the flexible chambers are inflatable and deflatable to adjust an inner dimension of the headrest to the patient's head.

* * * * *